US00PP36630P2

(12) United States Plant Patent
Heuger

(10) Patent No.: US PP36,630 P2
(45) Date of Patent: Apr. 22, 2025

(54) ***HELLEBORUS* PLANT NAMED 'HM 1222'**

(50) Latin Name: ***Helleborus ballardiae* X *Helleborus* x *hybridus***
Varietal Denomination: HM 1222

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/389,446

(22) Filed: Nov. 14, 2023

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
CPC ... A01H 5/02; A01H 5/12; A01H 5/00; A01H 6/72
See application file for complete search history.

(56) References Cited

PUBLICATIONS

Heuger 2023/2024 retrieved on Sep. 12, 2024 at https://www.gasagroup.com/Files/Images/corporate_website/Young%20Plants/Catalogues/Heuger-Helleborus.pdf, pp. 1-3, 8-9, 40-41, 58-59, 64-65. (Year: 2024).*

HobbyKafe forum *Helleborus*—2022/2023 retrieved on Sep. 12, 2024 at https://hobbykafe.com/forum/viewtopic.php?t=9702&start=320, 6 pp. (Year: 2023).*

* cited by examiner

*Primary Examiner* — June Hwu
(74) *Attorney, Agent, or Firm* — C. Anne Whealy

(57) ABSTRACT

A new and distinct cultivar of *Helleborus* plant named 'HM 1222', characterized by its upright to somewhat outwardly spreading and mounded plant habit; moderately vigorous to vigorous growth habit; dark green-colored leaflets with lighter green-colored venation; freely flowering habit; greenish white-colored flowers; and good garden performance.

1 Drawing Sheet

Figure 1:
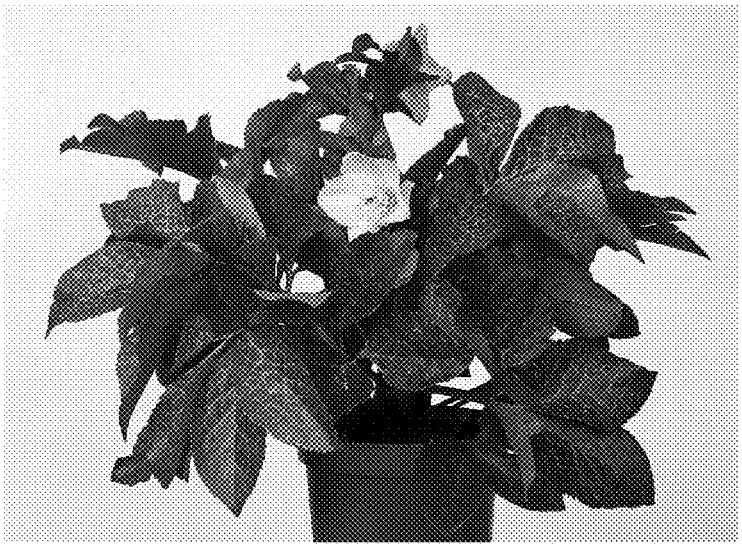

Botanical designation: *Helleborus ballardiae* X *Helleborus* x *hybridus*.
Cultivar denomination: 'HM 1222'.

CROSS-REFERENCED TO CLOSELY-RELATED APPLICATIONS

Title: *Helleborus* Plant Named 'HM 1224'
Inventor/Applicant: Josef Heuger
U.S. Plant Pat. No. 36,378

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 20, 2023, application number 2023/1379. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus ballardiae* X *Helleborus* x *hybridus* and hereinafter referred to by the name 'HM 1222'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in January, 2015 of a proprietary selection of *Helleborus ballardiae* identified as code number P482, not patented, as the female, or seed, parent and a proprietary selection of *Helleborus* x *hybridus* identified as code number O1633, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in January, 2017.

Asexual reproduction of the new *Helleborus* plant by in vitro axillary meristem culture in a controlled environment in Glandorf, Germany since April, 2017 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HM 1222'. These characteristics in combination distinguish 'HM 1222' as a new and distinct *Helleborus* plant:

1. Upright to somewhat outwardly spreading and mounded plant habit.
2. Moderately vigorous to vigorous growth habit.
3. Dark green-colored leaflets with lighter green-colored venation.
4. Freely flowering habit.
5. Greenish white-colored flowers.
6. Good garden performance.

Plants of the new *Helleborus* differ from plants of the female parent selection in the following characteristics:

1. Leaf venation of leaflets of plants of the new *Helleborus* is more distinct than leaf venation of leaflets of plants of the female parent selection.
2. Flowers of plants of the new *Helleborus* are greenish white in color whereas flowers of plants of the female parent selection are creamy white to pink in color.

Plants of the new *Helleborus* differ from plants of the male parent selection in the following characteristics:

1. Leaf venation of leaflets of plants of the new *Helleborus* is more distinct than leaf venation of leaflets of plants of the male parent selection.
2. Flowers of plants of the new *Helleborus* are greenish white in color whereas flowers of plants of the male parent selection are pink in color.

Plants of the new *Helleborus* can be compared to plants of *Helleborus ballardiae* X *Helleborus* x *hybridus* 'HM 1224', disclosed in a U.S. Plant Pat. No. 36,378. In side-by-side comparisons, plants of the new *Helleborus* differ primarily from plants of 'HM 1224' in flower color as plants of the new *Helleborus* have greenish white-colored flowers whereas plants of 'HM 1224' have dark red-colored flowers.

Plants of the new *Helleborus* can also be compared to plants of *Helleborus* x *ericsmithii* X *Helleborus* x *hybridus* 'COSEH 4500', disclosed in U.S. Plant Pat. No. 28,293. In side-by-side comparisons, plants of the new *Helleborus* differ primarily from plants of 'COSEH 4500' in leaf venation as leaf venation of leaflets of plants of the new *Helleborus* is more distinct than leaf venation of leaflets of plants of 'COSEH 4500'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph at the top of the sheet (FIG. 1) is a side perspective view of a typical flowering plant of 'HM 1222' grown in a container.

Figure 2:
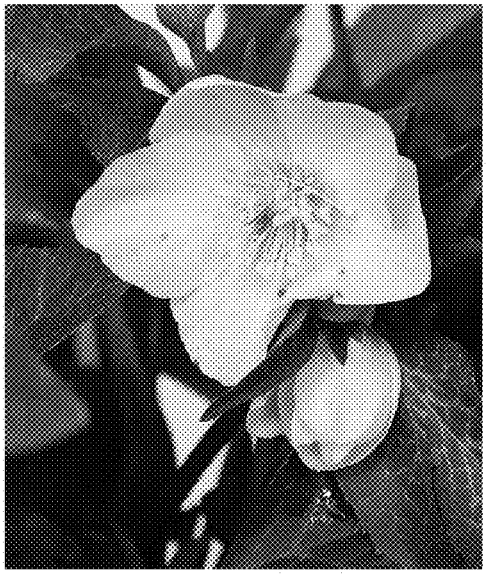

The photograph at the bottom of the sheet (FIG. 2) is a close-up view of a typical flowering plant of 'HM 1222'.

DETAILED BOTANICAL DESCRIPTION

The aforementioned photographs and following observations, measurements and values describe plants grown during the winter in 17-cm containers in a glass-covered greenhouse in Glandorf, Germany and under cultural practices typical of commercial *Helleborus* production. During the production of the plants, day temperatures ranged from 12 C to 32 C and night temperatures ranged from 5 C to 12 C. Plants were 48 weeks old when the photographs were taken and 14 months old when the description was taken. In the following description, color references are made to The Royal Horticultural Society Colour Chart, 2015 Edition, except where general terms of ordinary dictionary significance are used.

Botanical classification: *Helleborus ballardiae* X *Helleborus* x *hybridus* 'HM 1222'.

Parentage:

*Female, or seed, parent*.—Proprietary selection of *Helleborus ballardiae* identified as code number P482, not patented.

*Male, or pollen, parent*.—Proprietary selection of *Helleborus* x *hybridus* identified as code number O1633, not patented.

Propagation:

*Type*.—In vitro axillary meristem culture.

*Time to initiate roots, winter*.—About 55 days at temperatures about 12 C.

*Time to produce a rooted young plant, winter*.—About 170 days at temperatures ranging from about 4 C to 15 C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held within to slightly above the foliar plane; plant shape, roughly globular; moderately vigorous to vigorous growth habit and moderate growth rate.

*Plant height, soil level to top of foliar plane*.—About 28.7 cm.

*Plant height, soil level to top of flowers*.—About 32 cm.

*Plant diameter (area of spread)*.—About 55.9 cm.

Leaf description:

*Arrangement*.—Leaves arranged in a basal rosette; leaves palmately compound with typically five leaflets per leaf.

*Leaf length*.—About 18.2 cm.

*Leaf width*.—About 23 cm.

*Leaflet length*.—About 13.5 cm.

*Leaflet width*.—About 7.6 cm.

*Leaf shape*.—Palmate; roughly reniform in outline.

*Leaflet shape*.—Elliptic to ovate, occasionally obovate.

*Leaflet apex*.—Bluntly acute.

*Leaflet base*.—Attenuate.

*Leaflet margin*.—Serrate; moderately coarsely undulate.

*Leaflet texture and luster, upper surface*.—Smooth, glabrous; coriaceous and tough; moderately glossy.

*Leaflet texture and luster, lower surface*.—Smooth, glabrous; coriaceous and tough; matte to slightly glossy.

*Leaflet venation pattern*.—Pinnate and reticulate.

*Leaflet color*.—Developing leaflets, upper surface: Slightly darker than NN137A; towards the base, tinged with close to 183A to 183B; venation, close to 146D. Developing leaflets, lower surface: Close to 148A moderately to strongly tinged with close to N186C; venation, close to 187A. Fully developed leaflets, upper surface: Close to a blend of 139A and N189A; towards the base, tinged with close to 200B; venation, close to 138A. Fully developed leaflets, lower surface: Close to a blend of 147B and 148B; venation, close to N200A.

*Petioles*.—Length: About 20.9 cm. Diameter: About 6 mm by 7 mm. Strength: Strong. Texture and luster, upper and lower surfaces: Smooth, glabrous; moderately glossy. Color, upper surface: Close to 146B; moderately to heavily covered with fine dots, close to 183A and 187A. Color, lower surface: Close to 146C; moderately to heavily covered with fine dots, close to 187B and 187C.

Flower description:

*Flower shape and habit:*.—Single rotate bowl-shaped flowers arranged in panicles; freely flowering habit with about seven flowers per inflorescence and about 21 flowers and flower buds per plant; flowers face mostly outwardly to slightly nodding.

*Fragrance*.—None detected.

*Natural flowering season*.—Plants begin flowering about ten months after planting; plants flower naturally from late autumn into the winter in Germany.

*Flower longevity on the plant*.—About ten days; sepals persistent, other flower parts are not persistent.

*Flower buds*.—Length: About 2.6 cm. Diameter: About 1.5 cm. Shape: Elliptic to oblong. Texture and luster: Smooth, glabrous; matte. Color: Close to 145C to 145D; upper surface, strongly tinged with close to 182B to 182D.

*Inflorescence height* (*including peduncle*).—About 27.8 cm.

*Inflorescence diameter*.—About 15.3 cm.

*Flower diameter*.—About 8.1 cm.

*Flower depth*.—About 3.6 cm.

*Petals*.—All petals are transformed into nectaries.

*Sepals*.—Quantity and arrangement: About five, arranged in a single whorl. Length: About 4.7 cm. Width: About 4.2 cm. Shape: Broadly ovate to close to rhomboidal; slightly concave. Apex: Broadly and bluntly acute. Base: Cuneate. Margin: Entire; coarsely undulate. Texture and luster, upper surface: Smooth, glabrous; matte. Texture and luster, lower surface: Smooth, glabrous; matte to slightly glossy. Color: When opening, upper surface: Close to 157C to 157D. When opening, lower surface: Close to a blend of 145D and 157A; towards the margins and apex, close to 157C to 157D; towards the base, slightly tinged with close to 182B. Fully opened, upper surface: Lighter than 150D; towards the margins and apex, close to 157C to 157D; venation, similar to lamina colors; with subsequent development, color becoming closer to 150B slightly tinged with close to 182C. Fully opened, lower surface: Close to 150D tinged with close to 182B; towards the apex, tinged with close to 145D; venation, similar to lamina colors; with subsequent development, color becoming more strongly tinged with close to 182B.

*Flower bracts*.—Quantity per flower: Typically one. Length: About 10 cm. Width: About 7.4 cm. Shape: Ovate to broadly obovate. Apex: Acute to three-parted. Base: Truncate to cuneate. Margin: Proximally, entire, and distally, serrate; coarsely undulate. Color, upper surface: Darker than NN137A; venation, close to 144B and midvein, tinged with close to 187A. Color, lower surface: Close to 148A strongly tinged with close to 187A; midvein, close to 183A.

*Peduncles*.—Length: About 21.8 cm. Diameter: About 7.5 mm to 9 mm. Aspect: About 10 degrees from vertical. Strength: Strong. Texture and luster: Smooth, glabrous; moderately glossy. Color: Close to 146C to 146D; moderately to heavily covered with fine dots, close to 183C.

*Pedicels*.—Length: About 3.4 cm. Diameter: About 3 mm. Aspect: About 30 degrees from peduncle axis. Strength: Moderately strong. Texture and luster: Sparsely pubescent; slightly glossy. Color: Close to 146D to lighter than 146D; heavily covered with fine dots, close to 183D.

*Reproductive organs*.—Stamens: Quantity per flower: About 75. Filament length: About 1.6 cm. Filament color: Close to 157A. Anther shape: Double and broadly reniform; basifixed. Anther size: About 2 mm by 3 mm. Anther color: Close to 154C. Pollen amount: Sparse. Pollen color: Close to 4D to lighter than 4D. Pistils: Quantity per flower: About four to six. Pistil length: About 1.3 cm. Stigma diameter: About 0.3 mm. Stigma shape: Club-shaped. Stigma color: Close to 157A. Style length: About 1.25 cm. Style color: Close to 186A. Ovary color: Close to 145B. Nectaries (transformed petals): Quantity per flower: About 13 to 15. Length: About 1.2 cm. Diameter: About 3 mm. Shape: Tubular, flattened; apices, obtuse. Texture and luster, inner and outer surfaces: Smooth, glabrous; slightly glossy. Color, immature, inner and outer surfaces: Close to 145A. Color, mature, inner and outer surfaces: Close to 151B to 151C; towards the base, close to 152C; venation, similar to lamina colors; with subsequent development, color becoming closer to 153B and towards the base, close to 152B.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35 C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HM 1222' as herein illustrated and described.

* * * * *